United States Patent [19]

Watt et al.

[11] Patent Number: 5,707,231
[45] Date of Patent: Jan. 13, 1998

[54] ORTHODONTIC ASSEMBLY WITH REINFORCEMENT STRUCTURE

[75] Inventors: David E. Watt, Nederland, Colo.; Walter Schmidt, Auburn, Calif.

[73] Assignee: RMO, Inc., Denver, Colo.

[21] Appl. No.: 280,014

[22] Filed: Jul. 25, 1994

[51] Int. Cl.⁶ .................................................. A61C 7/12
[52] U.S. Cl. ........................................... 433/8; 433/9
[58] Field of Search ......................................... 433/8, 9

[56] References Cited

U.S. PATENT DOCUMENTS

| | | | |
|---|---|---|---|
| 3,930,311 | 1/1976 | Andrews | 32/14 |
| 4,219,617 | 8/1980 | Wallshein | 433/8 |
| 4,536,154 | 8/1985 | Garton, Jr. et al. | 433/8 |
| 4,717,341 | 1/1988 | Goldberg et al. | 433/9 |
| 4,954,080 | 9/1990 | Kelley et al. | 433/8 |
| 5,011,403 | 4/1991 | Sadoun et al. | 433/8 |
| 5,071,344 | 12/1991 | Wong et al. | 433/8 |
| 5,078,596 | 1/1992 | Carberry et al. | 433/8 |
| 5,232,361 | 8/1993 | Sachdeva et al. | 433/8 |
| 5,256,062 | 10/1993 | Griott | 433/8 |
| 5,267,855 | 12/1993 | Tuneberg | 433/9 |
| 5,295,823 | 3/1994 | Farzin-Nia et al. | 433/9 |
| 5,318,440 | 6/1994 | Adam et al. | 433/8 |
| 5,425,640 | 6/1995 | Scharf | 433/9 |

OTHER PUBLICATIONS

"Brinellium—A Harder, Stronger, and More Wettable Form of Aluminum Oxide", Mar./Apr. 1993, vol. 8, No. 3/4 pp. 44–45; *Technological Advances*.

Milewski, John V., "Efficient Use of Whiskers in the Reinforcement of Ceramics" *Advanced Ceramics*, vol. 1, No. 1, 1986, pp. 36–41.

*Primary Examiner*—David A. Wiecking
*Attorney, Agent, or Firm*—Sheridan Ross P.C.

[57] ABSTRACT

An orthodontic assembly including an orthodontic appliance and a region composed of a matrix material having a plurality of reinforcement structures distributed throughout, with some of the reinforcement structures being exposed on an exterior surface of the assembly, as well as an associated method of fabrication. In one embodiment, the entire orthodontic appliance is composed of the noted reinforcement structures and matrix material. In another embodiment, the noted region is actually a layer which is attached to a separately formed appliance, such as a bracket. Nonetheless, the reinforcement structures may be exposed in a variety of locations, such as on the base and/or arch slot. Moreover, this region may be formed by forming the appliance from the reinforcement structures and matrix material in a manner which produces skin on its exterior surface, and removing the skin from the desired areas to expose reinforcement structures partially contained within the matrix material.

32 Claims, 7 Drawing Sheets

ORTHODONTIC ASSEMBLY WITH REINFORCEMENT STRUCTURE

FIELD OF THE INVENTION

The present invention generally relates to the field of orthodontic assemblies and, more particularly, to orthodontic assemblies in which at least a part thereof incorporates reinforcement structures distributed preferably substantially uniformly throughout and at least partially suspended within a matrix material, and with a part of these reinforcement structures being exposed on an outer or exterior surface of the orthodontic assembly.

BACKGROUND OF THE INVENTION

Various types of orthodontic appliances have been developed over the years. These orthodontic appliances have been fabricated from a number of different materials depending upon the prioritization of the following types of considerations: strength of the material, bondability to teeth, resiliency, brittleness, expense, aesthetic qualities, structural stability, and ease of manufacture and maintenance.

Orthodontic brackets have been manufactured from various types of metals. Metal brackets provide a rigid structure for positioning an arch wire in a distorted configuration. The effort of the archwire to return to its passive shape urges the teeth into desired positions. Although metal brackets exhibit excellent strength characteristics, the manufacture of such brackets typically entails expensive machining of wrought metal or injection molding of metallic powders as bracket configurations become more complex. Further, with respect to bracket appearance, metal brackets do not satisfy a growing objective of many to match bracket color with tooth color.

Brackets have also been manufactured from various types of plastics. Plastic brackets can provide a more aesthetic appearance by closely matching bracket color with tooth color and upon selection of an appropriate adhesive exhibit an acceptable bond strength. Additionally, plastic brackets are relatively inexpensive and easy to fabricate. However, the wear resistance of plastic brackets is minimal and such brackets are prone to staining. Moreover, the strength characteristics of many plastic brackets are insufficient in certain applications. That is, plastic brackets often do not provide a sufficiently rigid structure for long term treatment and/or may be subject to undesired structural deformation (e.g., creep) when certain magnitude treatment forces are used. Consequently, certain treatment modalities are not possible using plastic brackets.

Ceramics have also been utilized in the manufacture of brackets. Ceramic brackets provide a strong and aesthetically pleasing orthodontic bracket. However, such ceramic brackets exhibit drawbacks with respect to their bonding characteristics and structural stability. Additionally, ceramic brackets can be brittle and abrasive if teeth contact the bracket.

Substantial development efforts have been and continue to be directed toward "improving" brackets and other orthodontic appliances formed from the above-noted materials. These efforts have included investigations utilizing combinations of materials in a single appliance. However, there continues to be a need for orthodontic appliances which show an overall improvement based upon the above-noted types of factors.

SUMMARY OF THE INVENTION

Accordingly, it is an object of the present invention to provide an orthodontic assembly in which the bond between the orthodontic appliance and the tooth is sufficient for orthodontic treatment.

Another object of the present invention is to provide an orthodontic assembly in which the interface between the arch wire and the orthodontic appliance is stable for orthodontic treatment and that will not degrade during the duration of treatment.

Another object of the present invention is to provide an orthodontic assembly which is both chemically and mechanically bondable to a tooth's surface.

Another object of the present invention is to provide an orthodontic assembly having strength and wear resistance for orthodontic treatment.

Another object of the present invention is to provide a process for fabricating an orthodontic assembly that satisfies the aforementioned objectives.

The present invention is generally directed toward an orthodontic assembly having an orthodontic appliance in which at least one region thereof is a material composed of reinforcement structures (e.g., fibers, whiskers, and/or spheres) distributed substantially and preferably uniformly throughout and at least partially suspended within a matrix material (e.g., plastics, metals, and ceramics) (e.g., the reinforcement structures are more than merely impregnated with the matrix material). More specifically, portions of at least some of these reinforcement structures are exposed on at least part of the exterior surface of the orthodontic appliance. The entire appliance may be formed from the noted matrix material and reinforcement structures, or a separate layer of the noted matrix material and reinforcement structures may be affixed to the desired area of a conventionally formed one-piece orthodontic appliance, or the appliance may be formed by attaching a separately formed orthodontic body and base, one or both of which may be formed from the noted matrix material and reinforcement structures.

Various geometries and sizes of reinforcement particles may be used in the above-described manner in the matrix material. For instance, the reinforcement structures may be whiskers/fibers of substantially the same size, spheres of substantially the same size, or a combination of such whiskers/fibers and spheres. In addition, the reinforcement structures may be two or more different size ranges of spherical reinforcement structures, and whiskers/fibers (in one or more size ranges) may also be used in this combination. These types of reinforcement structures may also assume a repeating packing geometry (e.g., a distribution which is repeated, predictable, and controllable), to provide an anisotropic structure, or may be randomly distributed in the matrix material to provide an isotropic structure.

In one embodiment, the above-noted orthodontic appliance has a base with a bonding surface which projects toward the patient's tooth. The above-noted region of matrix material and reinforcement structures is on/defines this bonding surface such that the exposed reinforcement structures provide a surface for interconnecting the appliance and tooth, for instance by using a bonding adhesive. In this case, not only is there a chemical bond between the bonding adhesive and the matrix material and/or reinforcement structures, but a mechanical bond as well via an interlocking relationship between the exposed reinforcement structures and the bonding adhesive. More specifically, some of the reinforcement structures are partially embedded within the matrix material and are exposed on the exterior surface. This defines a roughened or irregular surface on the base of the orthodontic appliance which provides a bonding surface which may be desirably engaged by the bonding adhesive. This bonding surface with the noted irregularities provides both an increased surface area for engagement by the bonding adhesive (i.e., an increased surface area for the chemical bond) and also provides for the noted interlocking relationship with the bonding adhesive and thus a mechanical bond.

As will be discussed below relating to methodologies associated with the present invention, the above-noted region with exposed reinforcement structures may be integrally formed with the entire orthodontic appliance. That is, the entirety of the orthodontic appliance is formed from the noted matrix material and reinforcement structures, again with some of these reinforcement structures being exposed on at least one outer surface of the appliance. Moreover, the remaining reinforcement structures will be totally contained and suspended within the matrix material. In this case, the reinforcement structures are multifunctional in that the embedded reinforcement structures which form the body of the appliance provide for a desired degree of "internal" strength (e.g., bulk material properties such as tensile and compressive strength), while, as noted, those which are exposed provide a surface for interfacing with the bonding adhesive. It will be appreciated that the noted bonding surface may be realized by forming a separate orthodontic base from the noted matrix material and reinforcement structures and appropriately attaching the same to a separately formed orthodontic body (e.g., formed from the same or a different material(s)). Moreover, it may be possible to provide the bonding surface by adhering a layer of reinforcement structures and matrix material in the form of a paste (e.g., such that at least some of the reinforcement structures are distributed throughout and suspended within the matrix material) onto a base of a separately formed orthodontic appliance, and thereafter curing this paste and further processing the same to expose the reinforcement structures in the manner discussed below.

In another embodiment, the above-noted orthodontic appliance has an arch slot and the above-noted region is on/defines the surfaces which define the arch slot (i.e., the floor and sidewalls). Since these surfaces define a portion of the perimeter or outer boundary of the orthodontic appliance, they are also referred to herein as an "exterior" surface. In this case, the exposed reinforcement structures in this region, which are again partially embedded within the matrix material and thus partially exposed, provide a roughened or irregular surface for slidably interfacing with the arch wire. As can be appreciated, these irregularities on the surface of the arch slot reduce the contact area between the arch wire and arch slot, and thereby the frictional interface therebetween. Benefits associated with the exposed reinforcement structures in the arch slot include increased wear and hardness over that of the matrix material alone.

In another embodiment, the above-noted layer(s) with exposed reinforcement structures may be formed by a method which includes forming a body of the orthodontic appliance from a material comprising a matrix material, such as the above-noted plastics, having a plurality of reinforcing structures distributed substantially entirely throughout. This forming process, however, results in the development of a "skin" on substantially the entire exterior surface of the orthodontic body. This "skin" may include a layer or zone of material which is substantially devoid of reinforcement structures, as well as an underlying layer or zone which is "lean" in reinforcement structures. Hereinafter, "skin" includes both of these zones. This skin may affect one or more aspects of the orthodontic body. Therefore, the method includes the step of removing this skin from at least a portion of the exterior surface of the body to expose a plurality of the noted reinforcement structures which, after removal of the skin, will remain partially embedded within the matrix material. The method contemplates the selective removal of the skin (e.g., removing the skin only from the base and/or arch slot surfaces, such as by using appropriate solvents) or removing substantially the entire skin (e.g., by tumbling the orthodontic body in an abrasive material). Based upon the above-definition of the "skin," it will be appreciated that there is not a "bright-line" boundary which separates the skin from the remainder of the orthodontic appliance. Nonetheless, the totality of the skin may be removed in the noted manner.

BRIEF DESCRIPTION OF THE DRAWINGS

Other features and advantages of the present invention will become apparent from the following Detailed Description taken in connection with the accompanying Drawings, in which.

DETAILED DESCRIPTION

Figure 1:
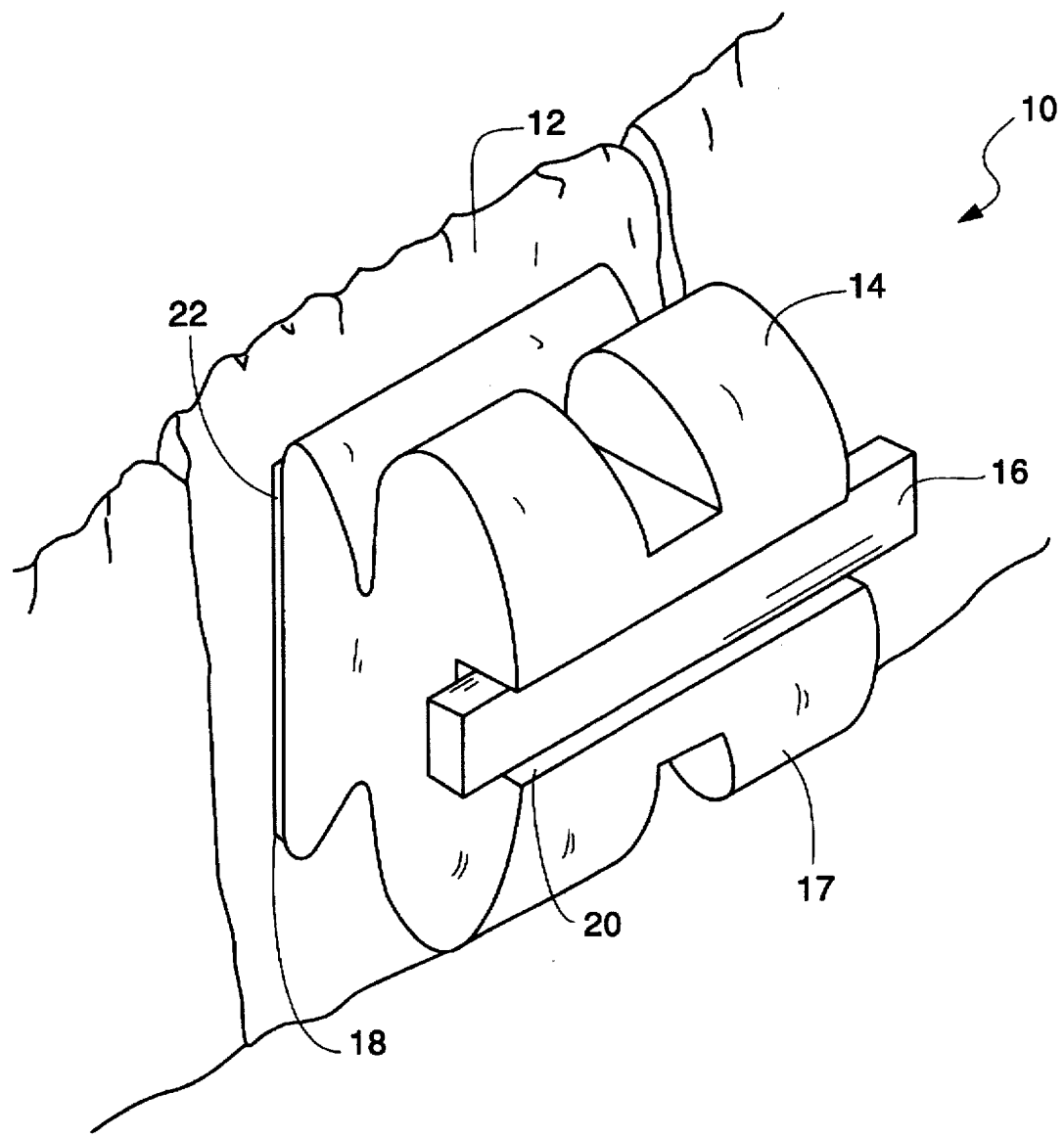
FIG. 1 is a perspective view of an orthodontic assembly in accordance with principles of the present invention.

The present invention will be described in relation to the accompanying drawings which assist in illustrating its various features. An orthodontic assembly 10 in accordance with principles of the present invention is illustrated in FIG. 1. Generally, the orthodontic assembly 10 includes an orthodontic appliance 14, an arch wire 16 for transmitting a treatment force to the appliance 14 and thus the corresponding tooth 12, and a bonding adhesive or interconnecting bond 22 for attaching the appliance 14 to the tooth 12 or enamel surface. The orthodontic appliance 14 has a base area 18, a portion of which projects toward the surface of the tooth 12, an arch slot 20 which receives the arch wire 16, and tie wings 17 for ligating the arch wire 16 within the slot 20 (ligatures not shown). The arch wire 16 can of course be adjusted according to the force required to conform the tooth 12 to the particular position desired. In this regard, the arch wire 16 may exert large forces upon the orthodontic appliance 14 within the limitations of orthodontic treatment.

Loads exerted upon the orthodontic appliance 14, such as by the arch wire 16, are communicated through the orthodontic appliance 14 to the tooth 12 in order to apply a corrective force upon the tooth 12. In this regard, the orthodontic appliance 14 itself and the bond strength between the orthodontic appliance 14 and the tooth 12 must both be strong in order to withstand such corrective forces, as well as other forces such as those produced by occlusion. The orthodontic assembly 10 addresses both bracket and bond strength through utilization of reinforcement structures distributed throughout a matrix material and by exposing some of these reinforcing structures on the bonding surface of the base area 18. The amount of matrix material is such that the reinforcement structures are more than merely coated or impregnated with the matrix material. Therefore, the interior reinforcement structures can be characterized as suspended within the matrix material.

The orthodontic appliance 10 is formed entirely from reinforcement structures 26 which are distributed substantially uniformly throughout a matrix material 30. Various configurations and/or sizes for reinforcement structures 26 within the matrix material 30 are illustrated in FIGS. 2A–2F. These particular packing configurations will be discussed in more detail below. However, generally the reinforcement structures 26 themselves and the strength of the bond between these reinforcement structures 26 and the matrix material 30 are believed to contribute to the overall strength or toughness of the appliance 10 (e.g., bulk material properties as noted).

Initially, a component of the matrix material 30 can be a plastic such as polycarbonate, clear polysulphone, polyetheretherketone (PEEK), polyethylene terephthalate (PETG) and acrylic. Moreover, a component of the reinforcement structures 26 or filler can be, for example, glass, titanium dioxide, feldspar, silicas, calcium carbonate, talc, micas, calcium silicates, metals, ceramics, and combinations thereof. Preferably, the reinforcement structures 26 are composed of, but not limited to, a ceramic material, such as zirconium oxide, aluminum oxide, magnesium oxide, and/or silicon oxide. More preferably, the reinforcement structures 26 are composed of oxygen saturated single crystal aluminum oxide. This specific aluminum oxide exhibits enhanced physical properties. For instance, the wettability of reinforcement structures 26 formed from oxygen saturated single crystal aluminum oxide is desirably high such that there is an increased chemical bond strength between the reinforcement structures 26 and the matrix material 30. Moreover, the noted oxygen saturated single crystal aluminum oxide also exhibits enhanced strength, hardness, and wear. Furthermore, an orthodontic appliance 14 fabricated with oxygen saturated single crystal aluminum oxide reinforcement structures 26 dispersed in a plastic matrix material 30 may exhibit tensile strengths more commonly associated with metal orthodontic appliances than those commonly associated with composite orthodontic appliances (e.g., 50 k psi minimum). These enhanced physical properties have been attributed to an excess of interstitial oxygen atoms which have been diffused into the crystal lattice structure. A detailed description of this oxygen saturated single crystal aluminum oxide may be found in U.S. patent application Ser. No. 08/231,451 filed Apr. 20, 1994 and entitled "OXYGENATED SINGLE CRYSTAL ALUMINUM OXIDE AND METHOD FOR PRODUCTION", which is a continuation in part of Ser. No. 07/937,975 entitled "MONOCRYSTALLINE ALUMINUM OXIDE WITH MODIFIED CRYSTAL LATTICE STRUCTURE", the entire disclosures of which is incorporated by reference in its entirety herein. Hereinafter, this particular type of aluminum oxide material is referred to as oxygen saturated aluminum oxide.

As noted, in order to produce a strong orthodontic appliance, the bond between each reinforcement structure 26 and the matrix material 30 must be strong as loads carried by the orthodontic appliance 14 are communicated through the matrix material 30 to the reinforcement structures 26 contained therein. In this regard, the reinforcement structures 26 can be coated with an appropriate bond enhancer in order to promote bonding between the reinforcement structures 26 and the matrix material 30. Such bond enhancers include organo-functional silanes. However, no bond enhancer is needed to promote bonding between the reinforcement structures 26 and matrix material 30 where the reinforcement structures 26 are composed of oxygen saturated aluminum oxide and the matrix material 30 is a plastic such as polycarbonate. Additionally, it is believed to be advantageous to utilize whiskers/fibers with low aspect ratios (i.e., the effective length divided by the effective diameter) (e.g., less than about 30). Such whiskers/fibers avoid tangling, bundling, and clumping with other fibers and thus produce homogeneous mixing.

In addition to selecting a material for the reinforcement structures 26, the dimension, shape, and amount of reinforcement structures 26 distributed in the matrix material 30 can be varied, depending upon the strength, bonding, and structural characteristics desired. With regard to general sizing of the reinforcement structures 26, in one embodiment, the reinforcement structures 26 have a dimension greater than about 1 micron. Preferably, the dimension measured is the diameter of the reinforcement structures 26. In this regard, the reinforcement structures 26 dispersed in the matrix material 30 of the orthodontic appliance 14 can be generally spherically-shaped and/or whisker/fiber-shaped.

With further regard to quantities of the reinforcement structures 26, in one embodiment the reinforcement structures 26 can occupy between about 9% to 95% by weight of the composite mixture, although it may not be practically possible to achieve this upper limit. More preferably, such reinforcement structures 26 occupy between about 10% to about 65% by weight of the composite mixture. Even more preferably, the reinforcement structures 26 occupy between about 10% to 45% by weight of the composite mixture.

With further regard to the shapes of the reinforcement structures 26 which may be utilized in the present invention, such may be whisker/fiber-shaped and/or generally spherically-shaped as noted. In the case of the whisker-shaped reinforcement structures 26 (i.e., single crystal), they may have cross-sections that are rectangular, cubic, ribbon-like, rhombohedral, triangular, circular, hexagonal, and parallelepiped. In the case of fiber-shaped reinforcement structures 26 (i.e., polycrystalline), they are typically of a generally circular cross-section. Moreover, the effective diameters of the whisker/fiber-shaped reinforcement structures 26 may range from about 1 micron to about 500 microns (whiskers generally being less than 10 microns in diameter), more preferably from about 1 micron to about 100 microns, and even more preferably from about 1 micron to about 10 microns. Furthermore, their lengths may range from about 10 microns to about 25 millimeters, more preferably from about 10 microns to about 500 microns, and even more preferably from about 10 microns to about 50 microns (e.g., the whiskers/fibers as used herein are not a continuous filament). In the case of the generally-spherical reinforcement structures 26, their effective diameters may range from about 0.5 micron to about 200 microns, more preferably from about 1 micron to about 100 microns, and even more preferably between about 1 micron and about 50 microns.

In addition to varying the shape, dimension, and amount of reinforcement structures 26, it is believed that packing configurations for reinforcement structures 26 in the matrix material 30 can be varied to produce stronger orthodontic appliances 14. For example, in one embodiment of the present invention, a selected amount of whisker/fiber-shaped reinforcement structures 26 can be distributed within an amount of the matrix material 30. In another embodiment of the present invention, generally spherically-shaped reinforcement structures 26 can be combined with whisker/fiber-shaped reinforcement structures 26 and distributed in a matrix material 30. Also, in another embodiment, generally spherically-shaped reinforcement structures 26 of similar or different diameters can be dispersed within the matrix material 30, alone or in combination with one or more sizes of whisker/fiber-shaped reinforcement structures 26.

Figure 2A:
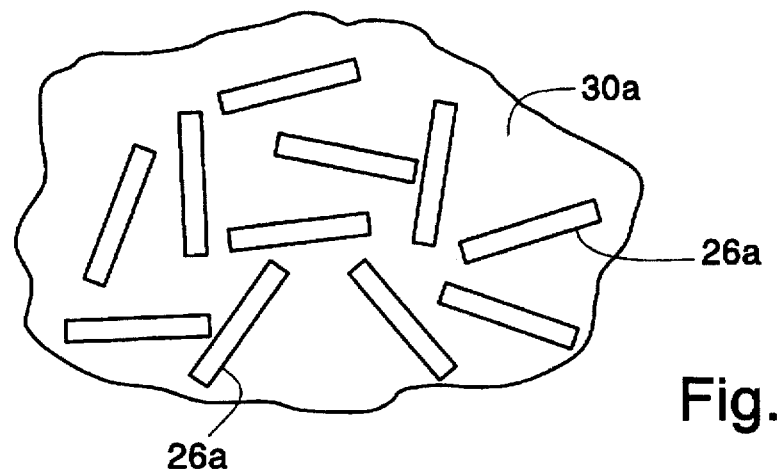
FIG. 2A is a micro-view of a whisker/fiber-based packing configuration which may be used for the orthodontic assembly of FIG. 1.

Referring to FIG. 2A, in one embodiment of the present invention, whisker/fiber-shaped reinforcement structures 26a are mixed within the matrix material 30a. These fiber-shaped reinforcement structures 26a may have cross-sections, lengths, and effective diameters within the above-noted ranges, and may be present in the above-described amounts.

Figure 2B:
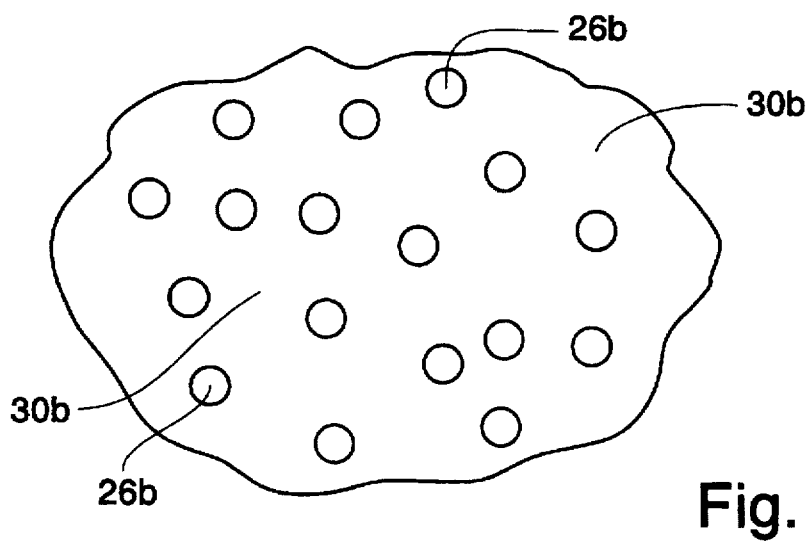
FIG. 2B is a micro-view of a sphere-based packing configuration which may be used for the orthodontic assembly of FIG. 1.
Figure 2C:
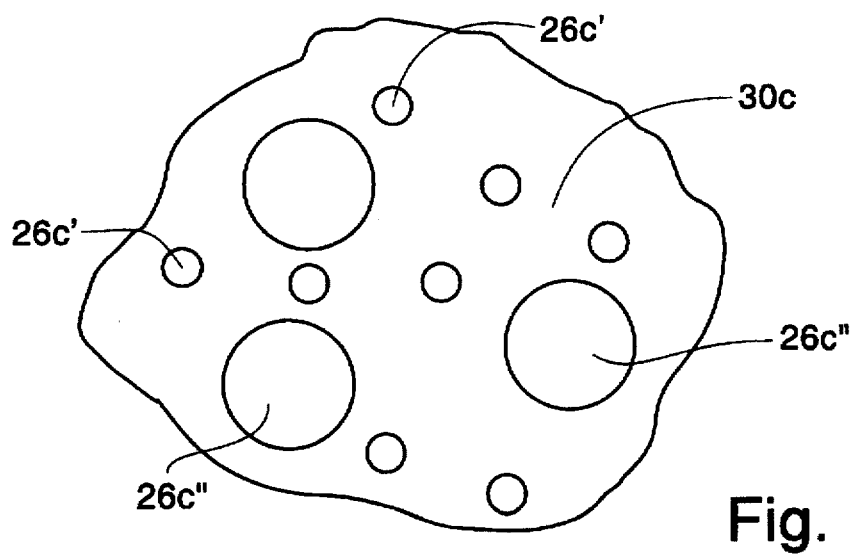
FIG. 2C is a micro-view of a bimodal, sphere-based packing configuration which may be used for the orthodontic assembly of FIG. 1.

Referring to FIG. 2B, in another embodiment of the present invention generally spherically-shaped reinforcement structures 26b are mixed with the matrix material 30b. The generally spherically-shaped reinforcement structures 26b may have a diameter in the above-noted ranges and be present in the above-noted amounts. A bimodal packing configuration in accordance with principles of the present invention is illustrated in FIG. 2C. Generally, small, generally spherically-shaped reinforcement structures 26c' and large, generally spherically-shaped reinforcement structures 26c" are combined with the matrix material 30c to produce a composite mixture for an orthodontic appliance. Generally, the small, generally spherically-shaped reinforcement structure 26c' are within a first size range, and the large, generally spherically-shaped reinforcement structures 26c" are within a second size range which is different from the first size range. In one embodiment, the small, generally spherically-shaped reinforcement structures 26c' measure between about 1 micron and about 6 microns in diameter, while the large, generally spherically-shaped reinforcement structures 26c" measure between about 20 microns and about 30 microns in diameter. More preferably, the small, generally spherically-shaped reinforcement structures 26c' measure from about 1 micron to about 2 microns in diameter, while the large, generally spherically-shaped reinforcement structures 26c" measure from about 23 microns to about 27 microns in diameter. Even more preferably, the small, generally spherically-shaped reinforcement structures 26c' measure approximately 2 microns in diameter, while the large, generally spherically-shaped reinforcement structures 26c" measure approximately 25 microns in diameter. The total amount of the reinforcement structures 26c', 26c" may be in the above-noted ranges. However, in one embodiment the reinforcement structures 26c' and 26c" account for about 30–33% by weight of the total, with about to about 33⅓% by weight being the small, generally spherically-shaped reinforcement structures 26c' and with about 66⅔% by weight being the large, generally spherically-shaped reinforcement structures 26c".

Figure 2D:
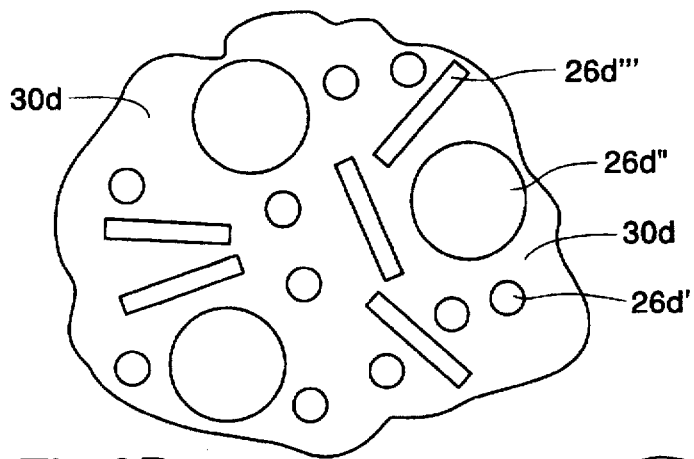
FIG. 2D is a micro-view of a trimodal, multi-sphere and whisker/fiber-based packing configuration which may be used for the orthodontic assembly of FIG. 1.

A trimodal packing configuration in accordance with the principles of the present invention is illustrated in FIG. 2D. In this embodiment, two size ranges of generally spherically-shaped reinforcement structures 26d' and 26d", as well as whisker/fiber-shaped reinforcement structures 26d''', are distributed throughout the matrix material 30d to produce a composite mixture. Generally, the sizes of the structures 26d', 26d", and 26d''' can be within the above-noted ranges. However, in one embodiment the small, generally spherically-shaped reinforcement structures 26d' measure between about 2 microns and about 10 microns in diameter (one size range) and the large, generally spherically-shaped reinforcement structures 26d" measure between about 20 microns and about 35 microns in diameter (another size range). More preferably, the small, generally spherically-shaped reinforcement structures 26d' measure between about 1 micron in diameter and about 4 microns in diameter, while the large, generally spherically-shaped reinforcement structures 26d" measure between about 23 microns and about 33 microns in diameter. Even more preferably, the small, generally spherically-shaped reinforcement structures 26d' measure between about 2 microns and about 4 microns in diameter, while the large, generally spherically-shaped reinforcement structures 26d" measure between about 25 microns and about 30 microns in diameter. With regard to the whisker/fiber-shaped reinforcement structures 26d''' of FIG. 2D, in one embodiment they range from about 1 microns to about 10 microns in diameter and between about 32 microns to about 64 microns in length. Even more preferably, the whisker/fiber-shaped reinforcement structures 26d''' measure about 3 microns and about 8 microns in diameter and about 40 microns to about 64 microns in length. With regard to the amounts of the reinforcement structures 26d', 26d", and 26d''', the total weight of such may be within the above-defined ranges. However, in one embodiment, the reinforcement structures 26d, 26d", and 26d''' present about 30–33% by weight of the total, with about 18% by weight of this amount being the small, generally spherically-shaped reinforcement structures 26d, with about 54% by weight of this amount being the large, generally spherically-shaped reinforcement structures 26d", and with about 28% by weight of this amount being the fiber-shaped reinforcement structures 26d'''.

Figure 2E:
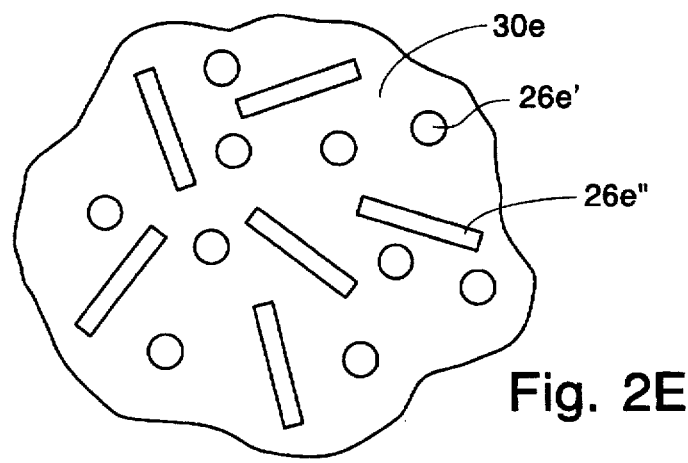
FIG. 2E is a micro-view of a bimodal, sphere and whisker/fiber-based packing configuration which may be used for the orthodontic assembly of FIG. 1.

Another packing configuration is illustrated in FIG. 2E in which generally spherically-shaped reinforcement structures 26e' and whisker/fiber-shaped reinforcement structures 26e" are distributed substantially throughout the matrix material 30e to produce a composite mixture. The generally spherically-shaped reinforcement structures 26e' preferably measure between about 20 microns and about 35 microns in diameter, and more preferably between about 25 microns and about 30 microns in diameter. The whisker/fiber-shaped reinforcement structures 26e" generally measure between about 1 microns and about 10 microns in diameter and less than about 100 microns in length, and more preferably measure between about 3 microns and about 8 microns in diameter and between about 40 microns and about 60 microns in length. The total weight of the reinforcement structures 26e' and 26e" may be within the above-noted ranges. However, in one embodiment the total weight of reinforcements structures 26e' and 26e" accounts for about 30–33% by weight of the total, with about 66⅔% by weight of this amount being the generally spherically-shaped reinforcement structures 26e' and with about 33⅓% by weight of this amount being the whisker/fiber-shaped reinforcement structures 26e".

The general packing configuration of FIG. 2E may also be used with smaller spherical particles. The generally spherically-shaped reinforcement structures 26e' preferably measure between about 1 microns and about 10 microns in diameter, and more preferably between about 3 microns and about 8 microns in diameter. The whisker/fiber-shaped reinforcement structures 26e" generally measure between about 1 microns and about 10 microns in diameter and about 100 microns in length, and more preferably measure between about 3 microns and about 8 microns in diameter and between about 40 microns and about 60 microns in length. The total weight of the reinforcement structures 26e' and 26e" may be within the above-noted ranges. However, in one embodiment, the total weight of reinforcements structures 26e' and 26e" accounts for about 30–33% by weight of the total, with about 66⅔% by weight being the generally spherically-shaped reinforcement structures 26e' and with about 33⅓% by weight being the whisker/fiber-shaped reinforcement structures 26e".

Figure 2F:
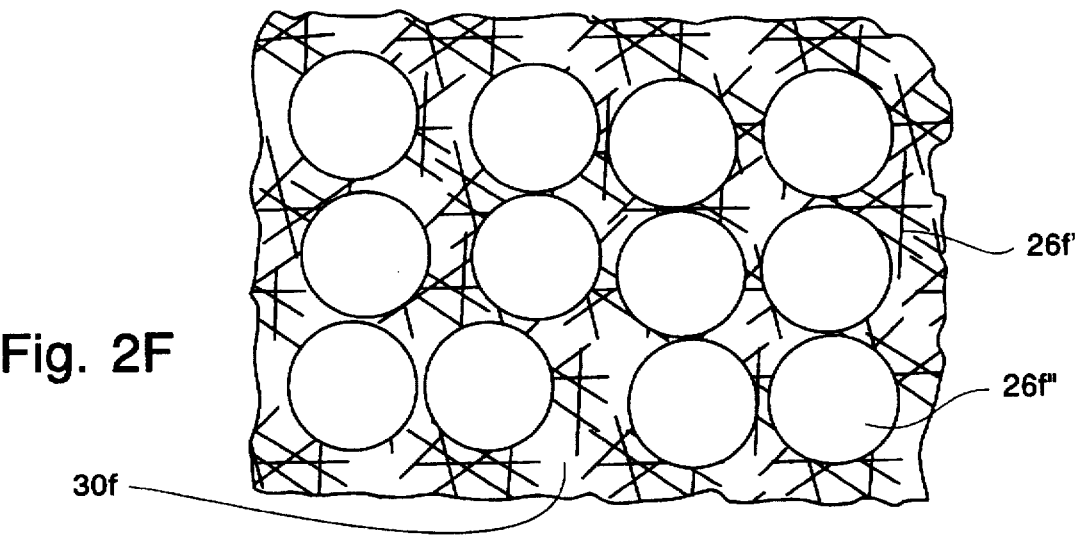
FIG. 2F is a micro-view of a bimodal, sphere and whisker/fiber-based, repeating order packing configuration which may be used for the orthodontic assembly of FIG. 1.

Another whisker/fiber-shaped and generally spherically-shaped reinforcement structure packing configuration is illustrated in FIG. 2F. Generally, the whisker/fiber-shaped reinforcement structures 26f' and the generally spherical reinforcement structures 26f" are in a predetermined position. This may be advantageous to define such an anisotropic structure which has difference properties in different directions. In this case, the sizes and amounts of the structures 26f' and 26f" may be as noted above with regard to the two FIG. 2E embodiments.

Figure 3A:
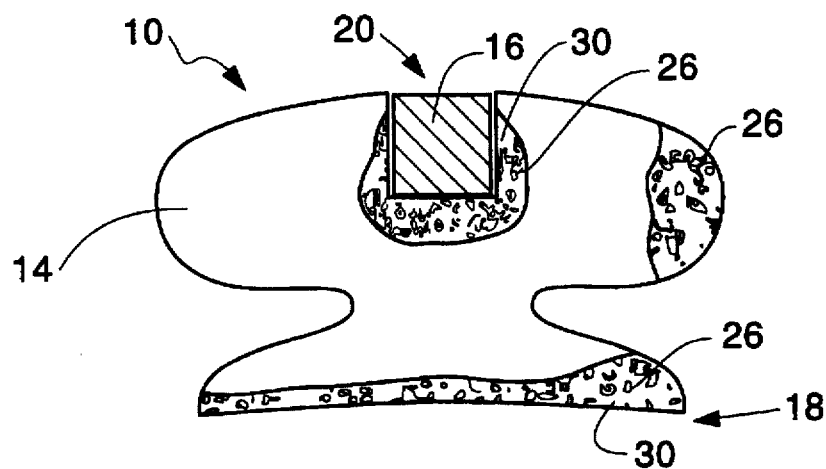
FIG. 3A is a partially broken-away end view (mesio-distally) of the orthodontic assembly of FIG. 1.
Figure 3B:
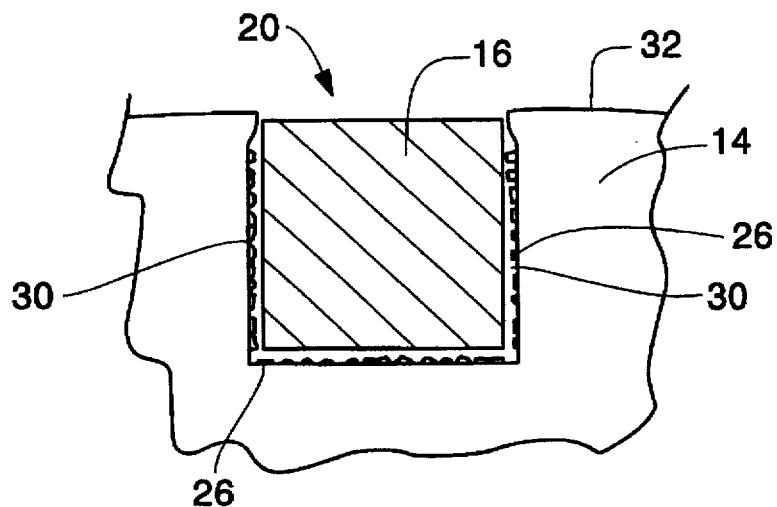
FIG. 3B is an enlarged end view (mesio-distally) of the arch slot area of orthodontic assembly of FIG. 3A.
Figure 3C:
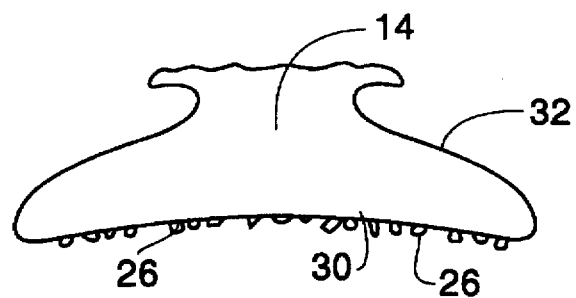
FIG. 3C is an enlarged end view (mesio-distally) of the base of the orthodontic assembly of FIG. 3.

As noted, the various reinforcement structures 26 described herein contribute to the strength of the appliance 10. That is, the entire orthodontic appliance 14 may be formed utilizing the types of packing configurations illustrated in FIGS. 2A–2E. However, the reinforcement structures 26 may also be used to affect other performance characteristics of the orthodontic assembly 10 as well. Referring to FIGS. 3A–3C, reinforcement structures 26 are illustrated as defining at least a portion of an exterior surface of the appliance 14. In the case of the appliance 14 in FIG. 3A, reinforcement structures 26 are exposed on the entirety of its exterior surface. However, for the appliance 14 illustrated in FIG. 3C, the reinforcement structures 26 only define a portion of this exterior surfaces, as will be discussed below. Referring to FIGS. 3A and 3C, a plurality of reinforcement structures 26 are exposed on the bonding surface of the base 18. That is, in addition to the reinforcement structures 26 which are totally embedded and suspended within and distributed homogeneously throughout the matrix material 30 of the appliance 14, some of such structures 26 are only partially embedded therein with parts thereof thereby being exposed. The reinforcement structures 26 in this area provide a surface for contributing to the bond strength between the orthodontic appliance 14 and the tooth 12 (FIG. 1).

Figure 4:
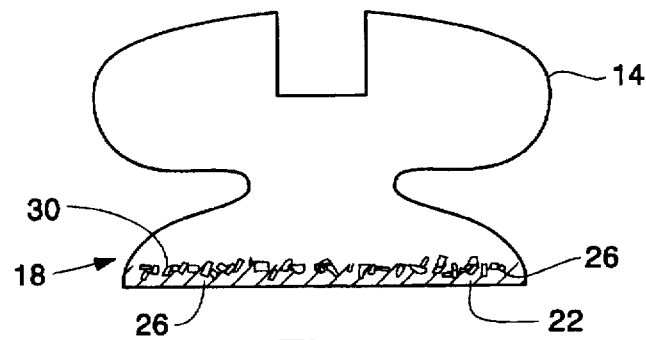
FIG. 4 is an end view (mesio-distally) of a bonding adhesive on the bonding surface of the base of the orthodontic assembly of FIG. 1.

Referring to FIG. 4, a bonding adhesive 22 (e.g., generally glass ionomer, light curing ionomer, luting cement, "Black Copper" cement, deposit bonding resins, zinc oxide cement, alumina EBA cement, veneer resins, and various methyl methacrylate compositions, and including RMO Mono-Lok 2™ One Step Bonding System and RMO Mono-Lok 2™ Light Cure Adhesive available from RMO, Inc. of Denver Colo.) may be used to attach the appliance 14 to the tooth 12. In this regard and as illustrated in FIG. 4, the bond between the adhesive 36 and the exposed reinforcement structures 26 has both a chemical and a mechanical aspect. As noted, where the reinforcement structures 26 are formed from oxygen saturated aluminum oxide, no bond enhancers are required due to the wettability of the material. Regardless of material selection, the exposed structures 26 provide a "roughened" surface for mechanical engagement with the bonding adhesive 22. However, there may also be a chemical bond between the exposed reinforcement structures 26 and the bonding adhesive 22, as well as between the reinforcement structures 26 and the matrix material 30.

As shown in FIGS. 3A–B, a layer of exposed reinforcement structures 26 can also be provided in an area of the arch slot 20. In the case of the appliance 14 of FIG. 3B, the reinforcement structures 26 only define a portion of its exterior surfaces as will be discussed below. Specifically, reinforcement structures 26 which are only partially embedded within the matrix material 30 are exposed in the arch slot 20 and define its surface which interfaces with the wire 16. Exposure of a part of each of a plurality of reinforcement structures 26 in an area of the arch slot 20 provides a roughened/irregular surface for interfacing with the arch wire 16. As noted, the benefits include a desired hardness and wear resistance, as well as a reduction in contact area between the wire 16 and slot 20.

Figure 5:
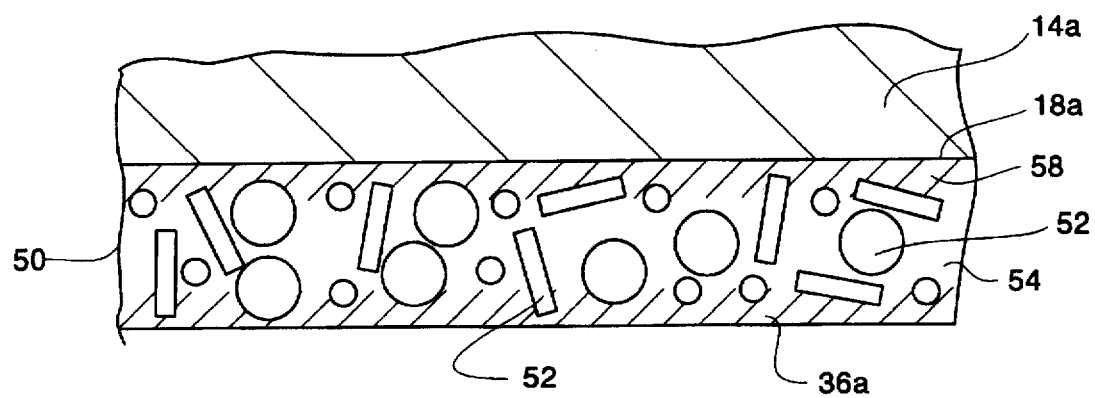
FIG. 5 is an end view (mesio-distally) of a layer of a matrix material and reinforcement structures separately applied to the area of the base of an orthodontic assembly.

Although the appliance 14 has been described as being formed entirely of the reinforcement structures 26 and matrix material 30, this need not be the case. For instance, a base may be formed from the noted reinforcement structures 26 and matrix material 30 and appropriately attached to a separately formed (from the same or dissimilar materials) orthodontic body (e.g., tie wings). Moreover, it may be possible for a layer of these structures and matrix material to be separately attached to the bonding surface of the base of a given orthodontic appliance and/or to its surfaces which define its arch slot in the form of a paste. In the event that a distribution of reinforcement structures in the matrix material may be achieved in the above-noted manner (e.g., some exposed on at least one exterior surface and some totally embedded/suspended within the matrix material), such is within the scope of the present invention. Referring to FIG. 5, the orthodontic appliance 14a is illustrated therein and which may be formed from various materials. In this case, a separate layer 50 of the reinforcement structures 52 similar to the structures 26 are distributed substantially uniformly throughout matrix material 54 which is similar to the matrix material 30. The layer 50 may be attached to an area on the base surface 18a of the orthodontic appliance 14a by appropriate adhesives 58. Once the layer 50 is on the appliance 14a it would be appropriately cured and attached to the tooth 12 by an adhesive 36a in the above-noted manner. In this curing process, it is anticipated that a skin will develop on the bonding surface which would then be removed in the manner discussed below to expose partially embedded reinforcement structures 52.

Figure 6B:
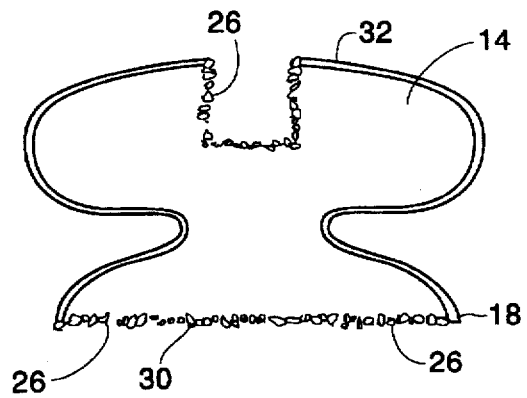
FIG. 6B is the orthodontic assembly of FIG. 6A after removal of matrix material skin only from selected areas of the orthodontic appliance.
Figure 6A:
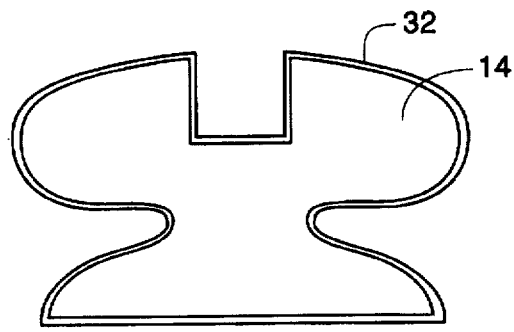
FIG. 6A is an end view (mesio-distally) of an orthodontic assembly of FIG. 1 with a finite layer of skin thereon for ease of illustration.
Figure 6C:
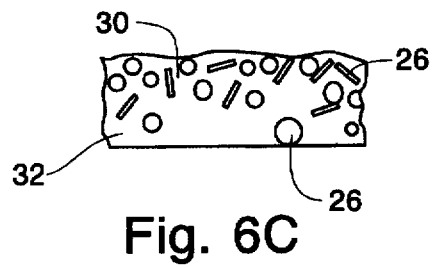
FIG. 6C is an enlarged view of the skin on the orthodontic assembly of FIG. 6A.

When the entire orthodontic appliance 14 is formed from the reinforcement structures 26 and matrix material 30, a thin layer 32 composed substantially of the matrix material 30 can cover its outer or exterior surfaces as illustrated in FIG. 6A. The skin 32 as described above (i.e., having a layer or zone which is substantially devoid of reinforcement structures 26 and/or a layer which is "lean" in structures 26) is illustrated in the enlargement of FIG. 6A which is presented in FIG. 6C. It is believed that this thin layer or skin 32 of matrix material 30 (as defined above) develops on outer surfaces of the orthodontic appliance 14 during the formation thereof (as well as when only a separate base and/or body is formed as noted, and when a paste of the reinforcement structures and matrix material is applied to an appliance and thereafter cured before attachment to the tooth). Accordingly, in the present invention and as illustrated in FIGS. 3B, 3C and 6B, the skin 32 of matrix material 30 is removed from selected areas of the outer surfaces of the orthodontic appliance 14. This removal of the skin 32 exposes a part of each of a plurality of reinforcement structures 26. In this regard, the reinforcement structures 26 in such an outer surface area are partially embedded in the matrix material 30 and are partially exposed. Some reinforcement structures 26 can even protrude from the select outer surfaces of the orthodontic appliance 14. One selected area for having exposed reinforcement structures 26 is the bonding surface of the base 18 the orthodontic appliance 14. In this region, the exposed reinforcement structures 26 provide a roughened surface for interfacing with the bonding adhesive 36. Another selected area is the exterior surfaces which define the arch slot 20. In this region, the exposed reinforcement structures 26 provide a roughened surface for interfacing with the arch wire 16 (e.g., for increased wear and hardness and surface contact reduction).

When only selected areas of a plastic skin 32 are removed from the appliance 14, solvents may be applied to the area in which a part of the reinforcement structures 26 are to be exposed. In a preferred embodiment where the matrix material 30 is polycarbonate, the solvent can be selected from the group consisting of tetrachloroethane, methylene chloride, ethylene dichloride, tetrahydrofuran, ammonium hydroxide (concentrate), potassium hydroxide (concentrate), sodium hydroxide (50% up), M-pyrol, 403 EX, or 1,1,2-trichloroethane. As can be appreciated, the type of solvent selected must be capable of dissolving the selected matrix material 30. Nonetheless, these solvents may be selectively applied by spraying, dipping, and brushing, utilizing masking techniques where required/desired.

Substantially all of the skin 32 may also be removed from all exterior surfaces of the appliance 14. In this regard, the above-noted types of solvents may be applied to the totality of the exterior surfaces of the appliance 14 in the above-noted manners. In addition, substantially the entire skin 32 may be removed by tumbling the appliance 14 within a tumbler (not shown). Such a tumbler can use water and appropriately sized tumbling media in order to remove the skin 32 to expose parts of the integrally formed reinforcement structures 26 on outer surfaces of the orthodontic appliance 14.

Figure 7:
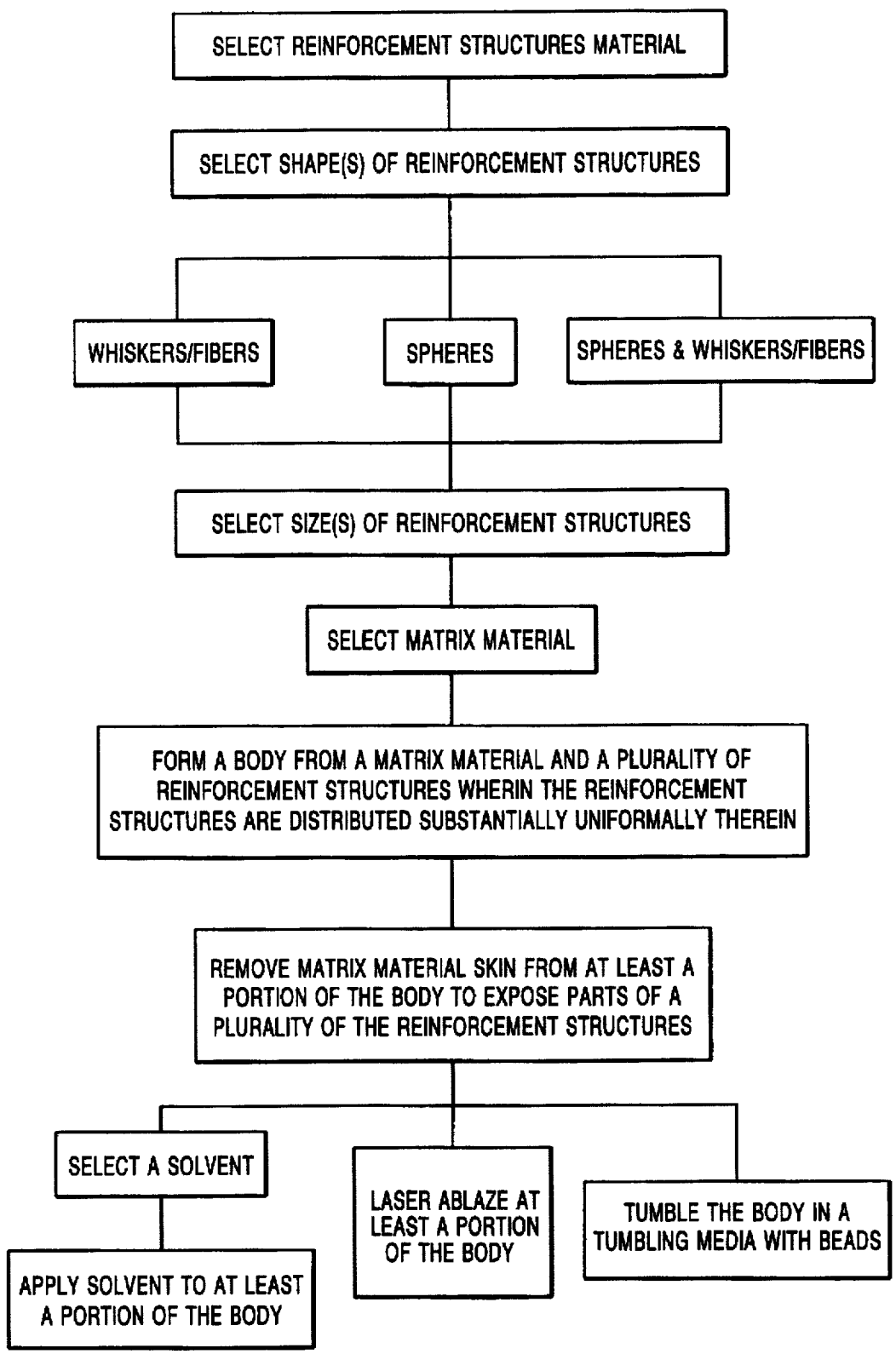
FIG. 7 is a flow chart which illustrates a method of making the present invention.

Methodologies associated with the present invention are schematically depicted in the flow chart of FIG. 7. Initially, the process includes selecting the material for the reinforcement structures 26. Additionally, the amount, dimension, and shape of the reinforcement structures 26 are to be selected. As noted, the reinforcement structures 26 may be generally spherically-shaped, whisker/fiber-shaped, and/or combinations thereof. These types of reinforcement structures 26 of the desired size and shape can be selected, provided, formed, or grown. In one embodiment of the present invention, the generally spherical shaped reinforcement structures 26 of a particular size can be produced by tumbling larger, randomly shaped chips of the selected reinforcement structures 26 in a spherical tumbler. The tumbling action not only reduces the reinforcement structures' 26 particulate size, but also shapes the chips into generally spherical particulates.

In another method of forming generally spherical structures 26, ceramic particulates or structures can be fed or propelled through a flame, produced, for example, by a flame spray gun. As the particulates travel through the flame in free space, the particulates partially melt. Partially melting the particulates in free space and allowing the particulates to cool as they fall through free space transforms the particulates into generally spherically-shaped reinforcement structures. For example, in one embodiment of the present invention, polycrystalline alumina can be fired at very high temperatures for a period of time to produce polycrystalline alumina of over 99% purity. This firing process eliminates impurities, such as binders, within the alumina that can effect the pourability of the alumina. Once fired, the polycrystalline alumina can be propelled through an oxygen based flame. The flame can be produced by an oxygen/hydrogen combination or an oxygen/acetylene combination. As the polycrystalline alumina travels in free space through the flame, the polycrystalline alumina completely melts to a liquid droplet and forms spherical reinforcement structures 26 of aluminum oxide that are generally translucent/transparent.

Ceramic fiber-shaped reinforcement structures 26 can be provided by growing such fibers with nuclei seeded gel on a ceramic substrate. In this process, small particulates of single crystal material is mixed with a sol gel and brushed on a ceramic substrate. Whiskers grow in repeating order shaped structures 26.

The type of matrix material 30 must also be selected such that composite mixture may be formed by the addition of the reinforcement structures 26 thereto, such as by blending or compounding. In an embodiment of the present invention, ceramic reinforcement structures 26 can be mixed with a plastic matrix material 30 such as polycarbonate as noted above. Once the composite mixture is produced, the orthodontic appliance 14 can be formed by molding or extrusion of the composite mixture. For instance, molding of an orthodontic appliance 14 can be accomplished by but not limited to injection molding or transfer molding.

In one embodiment of the present invention, the composite mixture of reinforcement structures 26 and matrix material 30 can be "gated" during the molding process in order to achieve a desired orientation of reinforcement structures 26 within the matrix material 30. For example, the velocity, mold temperature and volume of the flow of the composite material into the mold can be selected such that whisker/fiber-shaped reinforcement structures 26 within the orthodontic appliance 14 will be substantially parallel with or randomly oriented near an outer surface of the orthodontic appliance 14. In this regard, the orientation of reinforcement structures 26 in selected areas can be varied depending upon the bonding or structural characteristics desired.

As noted, during the molding process a thin layer or skin 32 of the matrix material 30 typically develops on outer surfaces of the orthodontic appliance 14. According to the present invention, this thin layer 32 of matrix material 30 can be removed from outer surfaces of an orthodontic appliance 14 in order to expose parts of a plurality of the reinforcement structures 26 distributed and integrally embedded in the orthodontic appliance 14. This removal may be done selectively to have only certain exterior surfaces of the appliance 14 be defined by exposed reinforcement structures 26, or the entire skin 32 may be removed. Moreover, removal of the skin 32 may be via solvents or tumbling or other appropriate methods.

Once an orthodontic appliance 14 has been formed and the thin layer 32 of matrix material 30 removed from the desired areas on the outer surface of the orthodontic appliance 14, an interconnection between the orthodontic appliance 14 and the tooth 12 can be selected, provided, and applied to the orthodontic appliance 14 on the bonding surface area of the base 18 of the orthodontic appliance 14. Preferably, an interconnection and/or orthodontic bonding adhesive 36 is applied to a surface area in the base 18 of the orthodontic appliance 14 where parts of a plurality of reinforcement structures 26 are exposed. In this regard, a chemical and mechanical bond between the adhesive and the reinforcement structures 26 may be achieved.

In one embodiment of the invention, the interconnection selected is a composite mixture of reinforcement structures 52 and matrix material 54 in the form of a layer 50 which is separately applied to the base 18a of an orthodontic appliance 14a with an adhesive 58. Applying such an interconnection to an area in the base of an orthodontic appliance can be accomplished by spatulating the composite mixture on the selected area of the base or by contacting an area of the base 18a of the orthodontic appliance 14a with the composite mixture. Where such an interconnection is utilized, a thin layer of matrix material can be removed chemically or mechanically from an outer surface of this interconnection in order to improve the bond between the interconnection and the tooth by exposing a layer of exposed reinforcing structures of matrix material, as noted.

The process for making an orthodontic assembly 10 can also include selecting, providing and/or positioning an arch wire 16 within the arch wire slot 20 of the orthodontic appliance 14. Preferably, the arch wire 16 contacts parts of each of a plurality of reinforcement structures 26 in the arch slot 20. In this regard, the arch wire 16 is positioned such that it interfaces with reinforcement structures 26 in the arch slot 20.

The foregoing description of the present invention has been presented for purposes of illustration and description. Further, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular applications or uses of the present invention. It is intended that the appended claims be construed to include alternative embodiments to the extent permitted by the prior art.

What is claimed is:

1. An orthodontic assembly, comprising:
an orthodontic appliance, comprising a first region comprising a matrix material and a plurality of reinforcement structures distributed throughout and suspended within substantially all of said matrix material whereby an amount of matrix material is more than to merely coat/impregnate said plurality of reinforcement structures, wherein said first region has a thickness greater than a largest dimension of each of said reinforcement structures and comprises at least a first surface area, wherein at least a part of at least some of said plurality of reinforcement structures are exposed on and thereby define at least a portion of said first surface area and extend beyond adjacently positioned matrix material to provide discontinuities on said first surface area, said first surface area being at least one of a surface of said orthodontic appliance on which a bonding adhesive is applied to attach said appliance to a tooth of an orthodontic patient and a surface which interfaces with another orthodontic appliance.

2. An orthodontic assembly as claimed in claim 1, wherein said matrix material is selected from the group consisting of plastics, metals, ceramics, and combinations thereof.

3. An orthodontic assembly as claimed in claim 1, wherein said matrix material is a polymer.

4. An orthodontic assembly as claimed in claim 3, wherein said polymer is a polycarbonate.

5. An orthodontic assembly as claimed in claim 1, wherein each said reinforcement structure comprises a first material selected from the group consisting of glass, titanium dioxide, feldspar, silicas, calcium carbonate, talc, micas, calcium silicates, metals, ceramics, and combinations thereof.

6. An orthodontic assembly as claimed in claim 5, wherein said first material consists of said ceramic which is selected from the group consisting of oxygen saturated aluminum oxide, magnesium oxide, silicon oxide, zirconium oxide, and combinations thereof.

7. An orthodontic assembly as claimed in claim 6, wherein said ceramic consists of said oxygen saturated aluminum oxide.

8. An orthodontic assembly as claimed in claim 1, wherein a first portion of said plurality of reinforcement structures are whiskers/fibers and a second portion of said plurality reinforcement structures are generally spherical.

9. An orthodontic assembly as claimed in claim 8, wherein each said whisker/fiber has a diameter ranging from about 3 microns to about 8 microns and a length ranging from about 40 microns to about 60 microns.

10. An orthodontic assembly as claimed in claim 8, wherein said second portion comprises a plurality of said reinforcement structures within a first size range and a plurality of said reinforcement structures within a second size range different from said first size range.

11. An orthodontic assembly as claimed in claim 1, wherein a first portion of said plurality of reinforcement structures each have a dimension greater than about 1 micron.

12. An orthodontic assembly as claimed in claim 1, wherein said plurality of reinforcement structures are each generally spherical.

13. An orthodontic assembly as claimed in claim 12, wherein a first portion of said plurality of reinforcement structures are within a first size range and a second portion of said plurality of reinforcement structures are within a second size range different from said first size range.

14. An orthodontic assembly as claimed in claim 13, wherein said first size range is a diameter ranging from about 20 microns to about 35 microns and said second size range is a diameter ranging from about 1 micron to about 4 microns.

15. An orthodontic assembly as claimed in claim 1, wherein said plurality of reinforcement structures are each whiskers/fibers.

16. An orthodontic assembly as claimed in claim 1, further comprising an interconnecting means for supportably interconnecting said orthodontic appliance to a tooth, wherein said interconnecting means interfaces with said first surface area.

17. An orthodontic assembly as claimed in claim 16, wherein said interconnecting means comprises an adhesive.

18. An orthodontic assembly, as claimed in claim 1, wherein said orthodontic appliance further comprises a base having a bonding surface and wherein said first region is separately attached to said bonding surface of said base, said orthodontic assembly further comprising a bonding adhesive applied to said first surface area whereby said assembly may be attached to a tooth.

19. An orthodontic assembly, as claimed in claim 1, wherein an entirety of said orthodontic appliance is formed from said matrix material and a plurality of said reinforcement structures are distributed throughout substantially all of said matrix material, whereby said orthodontic appliance and said first region are integrally formed.

20. An orthodontic assembly, as claimed in claim 1, wherein said orthodontic appliance comprises an arch slot, said first surface area comprising surfaces of said arch slot which interface with an arch wire.

21. An orthodontic assembly, as claimed in claim 1, wherein said first region consists essentially of said matrix material and said plurality of reinforcement structures.

22. An orthodontic assembly, as claimed in claim 1, wherein said orthodontic appliance comprises an arch slot and said first surface area defines at least a portion of said arch slot, said assembly further comprising an arch wire positioned in said arch slot, whereby said at least a part of at least some of said plurality of reinforcement structures engage said arch wire.

23. An orthodontic assembly as claimed in claim 1, wherein said surface which interfaces with said another orthodontic appliance is an arch slot.

24. An orthodontic assembly as claimed in claim 1, wherein said orthodontic appliance comprises said matrix material and said plurality of reinforcement structures, said first region being integrally formed with said orthodontic appliance, wherein said orthodontic appliance is made by the method of forming a body from said matrix material having said plurality of reinforcement structures distributed substantially uniformly throughout and suspended within substantially all of said matrix material, forming a skin on an entirety of an exterior surface of said body which is a portion of said matrix material which is substantially devoid of said reinforcement structures or which is lean in relation to an amount of said reinforcement structures present in remaining portions of said matrix material, and removing said skin from at least a portion of said body to provide said first surface area.

25. An orthodontic assembly, comprising:

an orthodontic appliance positionable on a tooth;

a base which interfaces with the tooth and an arch slot which receives an arch wire; and a first region having a first surface which defines at least a first part of an exterior surface of said orthodontic assembly, said first region comprising a matrix material and a plurality of reinforcement structures distributed substantially uniformly throughout and suspended within substantially all of said matrix material whereby an amount of said matrix material is more than to merely coat/impregnate said reinforcement structures, wherein a first portion of said plurality of reinforcement structures are substantially totally contained within said matrix material and wherein a second portion of said reinforcement structures are only partially contained within said matrix material whereby parts of said reinforcement structures of said second portion are exposed on said first surface and extend beyond adjacently positioned matrix material to provide discontinuities on said first surface, said first surface comprising at least one of said base and said arch slot.

26. An orthodontic assembly, as claimed in claim 25, wherein:

said first region is separately attached to said orthodontic appliance said first surface projecting toward the tooth and comprising said base.

27. An orthodontic assembly, as claimed in claim 25, wherein:

said first surface comprises said arch slot.

28. An orthodontic assembly, as claimed in claim 25, wherein:

said first region consists essentially of said matrix material and said plurality of reinforcement structures.

29. An orthodontic assembly, as claimed in claim 25, wherein:

said orthodontic appliance comprises said matrix material and said plurality of reinforcement structures, said first region being integrally formed with said orthodontic appliance.

30. An orthodontic assembly, as claimed in claim 25, further comprising:

a coating on a second part of said exterior surface, said first and second parts defining all of said exterior surface of said orthodontic assembly.

31. An orthodontic assembly, as claimed in claim 25, wherein:

said first surface defines both an exterior surface of said base which projects toward the tooth and an exterior surface of said arch slot.

32. An orthodontic assembly as claimed in claim 25, wherein said orthodontic appliance comprises said matrix material and said plurality of reinforcement structures, said first region being integrally formed with said orthodontic appliance, wherein said orthodontic appliance is made by the method of forming a body from said matrix material having said plurality of reinforcement structures distributed substantially uniformly throughout and suspended within substantially all of said matrix material, forming a skin on an entirety of an exterior surface of said body which is a portion of said matrix material which is substantially devoid of said reinforcement structures or which is lean in relation to an amount of said reinforcement structures present in remaining portions of said matrix material, and removing said skin from at least a portion of said body to provide said first surface area.

* * * * *